United States Patent [19]
Yeh et al.

[11] Patent Number: 6,125,194
[45] Date of Patent: Sep. 26, 2000

[54] METHOD AND SYSTEM FOR RE-SCREENING NODULES IN RADIOLOGICAL IMAGES USING MULTI-RESOLUTION PROCESSING, NEURAL NETWORK, AND IMAGE PROCESSING

[75] Inventors: Hwa-Young M Yeh, Potomac; Yuan-Ming F Lure, Rockville; Jyh-Shyan Lin, Derwood, all of Md.

[73] Assignee: Caelum Research Corporation, Rockville, Md.

[21] Appl. No.: 09/018,789

[22] Filed: Feb. 4, 1998

Related U.S. Application Data

[63] Continuation-in-part of application No. 08/917,821, Aug. 28, 1997, and a continuation-in-part of application No. 08/597,736, Feb. 6, 1996, abandoned.

[51] Int. Cl.[7] .................................................. G06K 9/00
[52] U.S. Cl. ............................................................ 382/132
[58] Field of Search .................................... 382/132, 156, 382/173, 257, 128, 171, 294, 130, 224; 378/37; 128/922

[56] References Cited

U.S. PATENT DOCUMENTS

| | | | |
|---|---|---|---|
| 4,907,156 | 3/1990 | Doi et al. | 364/413.13 |
| 5,289,374 | 2/1994 | Doi et al. | 364/413.13 |
| 5,463,548 | 10/1995 | Asada et al. | |
| 5,598,481 | 1/1997 | Nishikawa et al. | 382/130 |
| 5,857,030 | 1/1999 | Gaborski et al. | 382/132 |
| 5,873,824 | 2/1999 | Doi et al. | 600/408 |

OTHER PUBLICATIONS

"Artificial convolution neural network techniques for lung nodule detection", by Lo, Lou, Lin, Freedman et al. IEEE Trans. Med. Image. vol. 14, pp. 711–718, Dec. 1, 1995.

Y.S.P., Chiou, Y.M.F. Lure, & P.A. Ligomenides. "Neural Network Image Analysis and Classification in Hybrid Lung Nodule Detection (HLND) System". Neural Networks for Processing III Proceedings of the 1993 IEEE–SP Workshop, pp. 517–526.

M.L. Giger. "Computerized Scheme for the Detection of Pulmonary Nodules". Image Processing VI, IEEE Engineering in Medicine & Biology Society. 11th Annual International Conference (1989).

*Primary Examiner*—Andrew W. Johns
*Assistant Examiner*—Shervin Nakhjavan
*Attorney, Agent, or Firm*—Venable; Robert Kinberg; Jeffrey W. Gluck

[57] ABSTRACT

An automated detection method and system improve the diagnostic procedures of radiological images containing abnormalities, such as lung cancer nodules. The detection method and system use a multi-resolution approach to enable the efficient detection of nodules of different sizes, and to further enable the use of a single nodule phantom for correlation and matching in order to detect all or most nodule sizes. The detection method and system use spherical parameters to characterize the nodules, thus enabling a more accurate detection of non-conspicuous nodules. A robust pixel threshold generation technique is applied in order to increase the sensitivity of the system. In addition, the detection method and system increase the sensitivity of true nodule detection by analyzing only the negative cases, and by recommending further re-assessment only of cases determined by the detection method and system to be positive. The detection method and system use multiple classifiers including back propagation neural network, data fusion, decision based pruned neural network, and convolution neural network architecture to generate the classification score for the classification of lung nodules. Such multiple neural network architectures enable the learning of subtle characteristics of nodules to differentiate the nodules from the corresponding anatomic background. A final decision making then selects a portion of films with highly suspicious nodules for further reviewing.

28 Claims, 12 Drawing Sheets

METHOD AND SYSTEM FOR RE-SCREENING NODULES IN RADIOLOGICAL IMAGES USING MULTI-RESOLUTION PROCESSING, NEURAL NETWORK, AND IMAGE PROCESSING

This application is a continuation-in-part of U.S. application Ser. No. 08/917,821, filed Aug. 28, 1997, and a continuation-in-part of U.S. application Ser. No. 08/597,736, filed Feb. 6, 1996, now abandoned.

BACKGROUND OF THE INVENTION

1. Field of the Invention

The present invention relates to methods and systems for the digital processing of radiological images, and it more specifically relates to an automated method and system for the re-screening and detection of abnormalities, such as lung nodules in radiological chest images using multi-resolution processing, digital image processing and artificial neural networks.

2. Background Art

Lung cancer is the leading type of cancer in both men and women worldwide. Early detection and treatment of localized lung cancer at a potentially curable stage can significantly increase the patients' survival rate. Studies have shown that approximately 68% of retrospectively detected lung cancers were detected by one reader and approximately 82% were detected with an additional reader as a "second-reader". A long-term lung cancer screening program conducted at the Mayo Clinic found that 90% of peripheral lung cancers were visible in small sizes in retrospect, in earlier radiographs.

Among the common detection techniques, such as chest X-ray, analysis of the types of cells in sputum specimens, and fiber optic examination of bronchial passages, chest radiography remains the most effective and widely used method. Although skilled pulmonary radiologist can achieve a high degree of accuracy in diagnosis, problems remain in the detection of the lung nodules in chest radiography due to errors that cannot be corrected by current methods of training even with a high level of clinical skill and experience.

An analysis of the human error in diagnosis of lung cancer revealed that about 30% of the misses were due to search errors, about 25% of the misses were due to recognition errors, and about 45% of the misses were due to decision-making errors. Reference is made to Kundel, H. L., et al., "Visual Scanning, Pattern Recognition and Decision-Making in Pulmonary Nodule Detection", Investigative Radiology, May–June 1978, pages 175–181, and Kundel, H. L., et al., "Visual Dwell Indicated Locations of False-Positive and False-Negative Decisions", Investigative Radiology, June 1989, Vol. 24, pages 472–478, which are incorporated herein by reference. The analysis suggested that the miss rates for the detection of small lung nodules could be reduced by about 55% with a computerized method. According to the article by Stitik, F. P., "Radiographic Screening in the Early Detection of Lung Cancer", Radiologic Clinics of North America, Vol. XVI, No. 3, December 1978, pages 347–366, which is incorporated herein by reference, many of the missed lesions would be classified as T1M0 lesions, the stage of non-small cell lung cancer that Mountain, C. F. "Value of the New TNM Staging System for Lung Cancer", 5$^{th}$ World Conference in Lung Cancer Chest, 1989 Vol. 96/1, pages 47–49, which is incorporated herein by reference, indicates has the best prognosis (42%, 5 year survival). It is this stage of lung cancer, with lesions less than 1.5 cm in diameter, and located outside the hilum region that need to be detected usually by a radiologist.

Commputerized techniques, such as computer aided diagnosis (CAD), have been introduced to assist in the diagnosis of lung nodules during the stage of non-small cell lung cancer. The CAD technique required the computer system to function as a second physician to double check all the films that a primary or first physician has examined. Reduction of false positive detection is the primary objective of the CAD technique in order to improve detection accuracy.

Several CAD techniques using digital image processing and artificial neural networks have been described in numerous publications, examples of which are the following, which are incorporated herein by reference:

U.S. Pat. No. 4,907,156 to Doi et al. describes a method for detecting and displaying abnormal anatomic regions existing in a digital X-ray image. A single projection digital X-ray image is processed to obtain signal-enhanced image data with a maximum signal-to-noise ratio (SNR) and is also processed to obtain signal-suppressed image data with a suppressed SNR. Then, difference image data are formed by subtraction of the signal-suppressed image data from the signal-enhanced image data to remove low-frequency structured anatomic background, which is basically the same in both the signal-suppressed and signal-enhanced image data. Once the structured background is removed, feature extraction, is formed. For the detection of lung nodules, pixel thresholding is performed, followed by circularity and/or size testing of contiguous pixels surviving thresholding. Threshold levels are varied, and the effect of varying the threshold on circularity and size is used to detect nodules. For the detection of mammographic microcalcifications, pixel thresholding and contiguous pixel area thresholding are performed. Clusters of suspected abnormalities are then detected. However, the algorithm described in the Doi et al. patent seems to reduce false positive rates at the expense of missing several true nodules. This prior art is limited in detection of nodules with size larger than its pre-selected size—1.5 cm. This prior art will also reduce the sensitivity by selecting fixed CDF thresholds (e.g., 97%, 94%, 91%, etc.) since some true nodules will be eliminated during this thresholding process. The algorithm described in the Doi et al. patent utilizes a single classifier (a decision tree classifier) which possesses limited performance compared to multiple classification schemes presented below. The use of a decision tree classifier performs classification in eliminating true positives in sequential way, hence it is easy to eliminate potential nodules in the first decision node even if the rest of the decision criteria are satisfied. Another important drawback in this prior art is that physician has to examine every film with both true and false positives identified by the CAD system, such that the time spent on the diagnosis increases dramatically.

U.S. Pat. No. 5,463,548 to Asada et al. describes a system for computer-aided differential diagnosis of diseases, and in particular, computer-aided differential diagnosis using neural networks. A first design of the neural network distinguishes between a plurality of interstitial lung diseases on the basis of inputted clinical parameters and radiographic information. A second design distinguishes between malignant and benign mammographic cases based upon similar inputted clinical and radiographic information. The neural networks were first trained using a hypothetical database made up of hypothetical cases for each of the interstitial lung diseases and for malignant and benign cases. The performance of the neural network was evaluated using receiver operating characteristics (ROC) analysis. The decision performance of the neural network was compared to experienced radiologists and achieved a high performance comparable to that of the experienced radiologists. The neural network according to the invention can be made up of a single network or a plurality of successive or parallel networks. The neural network according to the invention can also be interfaced to a computer which provides computerized automated lung texture analysis to supply radiographic input data in an automated manner. However Asada's method seems limited to the detection of lung diseases but not lung cancer, which present different symptoms.

Y. S. P. Chiou, Y. M. F. Lure, and P. A. Ligomenides, "Neural Network Image Analysis and Classification in Hybrid Lung Nodule Detection (HLND) System", Neural Networks for Processing III Proceedings of the 1993 IEEE-SP Workshop, pp. 517–526. The chiou et al. article described a Hybrid Lung Nodule Detection (HLND) system based on artificial neural network architectures, which is developed for improving diagnostic accuracy and speed of lung cancerous pulmonary radiology. The configuration of the HLND system includes the following processing phases: (1) pre-processing to enhance the figure-background contrast; (2) quick selection of nodule suspects based upon the most pertinent feature of nodules; and (3) complete feature space determination and neural classification of nodules. The Chiou et al. article seems to be based on U.S. Pat. No. 4,907,156 to Doi et al., but adds a neural network approach. The Chiou et al. system includes similar shortcoming as the Doi et al. system described in U.S. Pat. No. 4,907,156.

S. C. Lo, J. S. Lin, M. T. Freedman, and S. K. Mun, "Computer-Assisted Diagnosis of Lung Nodule Detection Using Artificial Convolution Neural Network", Proceeding of SPIE Medical Imaging VI, Vol. 1898, 1993. This article describes nodule detection methods using a convolutional neural network consisting of a two-dimensional connection trained with a back propagation learning algorithm, in addition to thresholding and circularity calculation, morphological operation, and a 2-D sphere profile matching technique. The use of a very complicated neural network architecture, which was originally developed for optical character recognition in binary images, the lengthy training time, and the lack of focus on the reduction of false positives, render the published nodule detection methods impractical. This prior art also possesses similar drawback as the Doi et al. system described in U.S. Pat. No. 4,907,156.

S. C. Lo, S. L. Lou, S. Lin, M. T. Freedman, and S. K. Mun, "Artificial convolution neural network techniques for lung nodule detection", IEEE Trans. Med. Imag. Vol 14, pp 711–718, 1995. This article describes nodule detection methods using a convolution neural network consisting of a two-dimensional connection trained with a back propagation learning algorithm, in addition to thresholding and circularity calculation, morphological operation, and a 2-D sphere profile matching technique. This prior art also possesses similar drawback as the Doi et al. system and that described in Lo, et al., 1993.

J-S Lin, P. Ligomenides, S-C B. Lo, M. T. Freedman, S. K. Mun, "A Hybrid Neural-Digital Computer Aided Diagnosis System for Lung Nodule Detection on Digitized Chest Radiographs", Proc. 1994 IEEE Seventh Symp. on Computer Based Medical Systems, pp. 207–212, describes a system for the detection and classification of cancerous lung nodules utilizing image processing and neural network. However, the system described in this article suffers from similar shortcomings as the system described in the Lo et al. article.

M. L. Giger, "Computerized Scheme for the Detection of Pulmonary Nodules", Image Processing VI, IEEE Engineering in Medicine & Biology Society, 11$^{th}$ Annual International Conference (1989), describes a computerized method to detect locations of lung nodules in digital chest images. The method is based on a difference-image approach and various feature-extraction techniques including a growth test, a slope test, and a profile test. The aim of the detection scheme is to direct the radiologist's attention to locations in an image that may contain a pulmonary nodule, in order to improve the detection performance of the radiologist. However, the system described in the article suffers from similar shortcomings as the system described in U.S. Pat. No. 4,907,156 to Doi et al.

SUMMARY OF THE INVENTION

One aspect of the present invention is to provide an automated method and system for improving diagnostic procedures of radiological images. The invention further enables the detection of lung nodules in radiological chest images using multi-resolution approach, digital image processing and artificial neural networks, and further enables the re-screening of radiographic chest images which were previously identified as negative by a radiologist. The invention can also be used for re-screening other conditions and diseases, including but not limited to microcalcification clusters, masses, and tumors of mammogram images.

The automated method and system of the present invention use multiple phases of multi-resolution processing, digital image processing and artificial neural networks to eliminate false positives, thus increasing detection accuracy. Once image data is acquired from a radiological chest image, the data is subjected to a multi-phase digital image processing technique to initially identify several suspect regions. First, during image enhancement phase, object-to-background contrast of the data is enhanced using multi-resolution matching technique. Next, during the quick selection phase, the data is subjected to sphericity testing, involving examination of circularity parameters of each grown region in a sliced (thresholding) image obtained from a series of pixel threshold values, and segmentation of suspect object blocks to preliminarily select nodule candidates. The pixel threshold values are derived based on the desired suspect nodule area (SNA) number and size, signal-to-nose ratio (SNR) of the image, and CDF of image in order to have maximal sensitivity. In the classification phase, data is processed using both feature parameter based and image area based classifiers. Both classifiers are implemented with neural network architectures: a back propagation neural network, a decision tree based pruned neural network and a convolution neural network. The detection results from these classifiers are integrated in a data fusion center to obtain the optimal classification score. Several different anatomic structures as well as true nodule are used as training classes to develop neural network classifiers. In the final phase, the decision making phase, the suspect nodules are analyzed using prevalence rate, risk factor, and system performance to determine portions of the films for further reviewing. The use of these multiple resolution, multiple classifiers, and presentation of portions of highly suspect films for physician's final diagnosis eliminates a high number of false positives experienced using prior art techniques and increases the detection accuracy.

The method and procedure of the present invention further enable medical diagnoses for re-screening of lung nodules in the radiographic chest images wherein a physician first examines the screen film of the chest X-ray to identify negative films, i.e., absence of lung nodules. The negative films are then processed by a computer re-screening unit of the present invention to identify potential lung nodules. The computer-identified "review" films, containing suspect lung nodules, are sent back to the physician for a final decision. The computer aided device or re-screen unit includes an image input unit, for example, a laser film scanner, a detection unit, and a display unit. The scanner digitizes the chest X-ray films into digital image data. The detection unit possesses advanced image processing capabilities to detect the lung nodules in the digital images. The display unit presents the positive films of the detection results as references for the physician's diagnosis. The use of re-screening methods achieves high detection accuracy by reducing false negatives.

BRIEF DESCRIPTION OF THE DRAWINGS

The features of the present invention and the manner of attaining them will become apparent and the invention itself will be understood by reference to the following description and the accompanying drawings, wherein.

Similar numerals refer to similar elements in the drawings. It should be understood that the sizes of the different components in the figures may not be in exact proportion, and are shown for visual clarity and for the purpose of explanation.

DETAILED DESCRIPTION OF THE PREFERRED EMBODIMENTS

Figure 1:
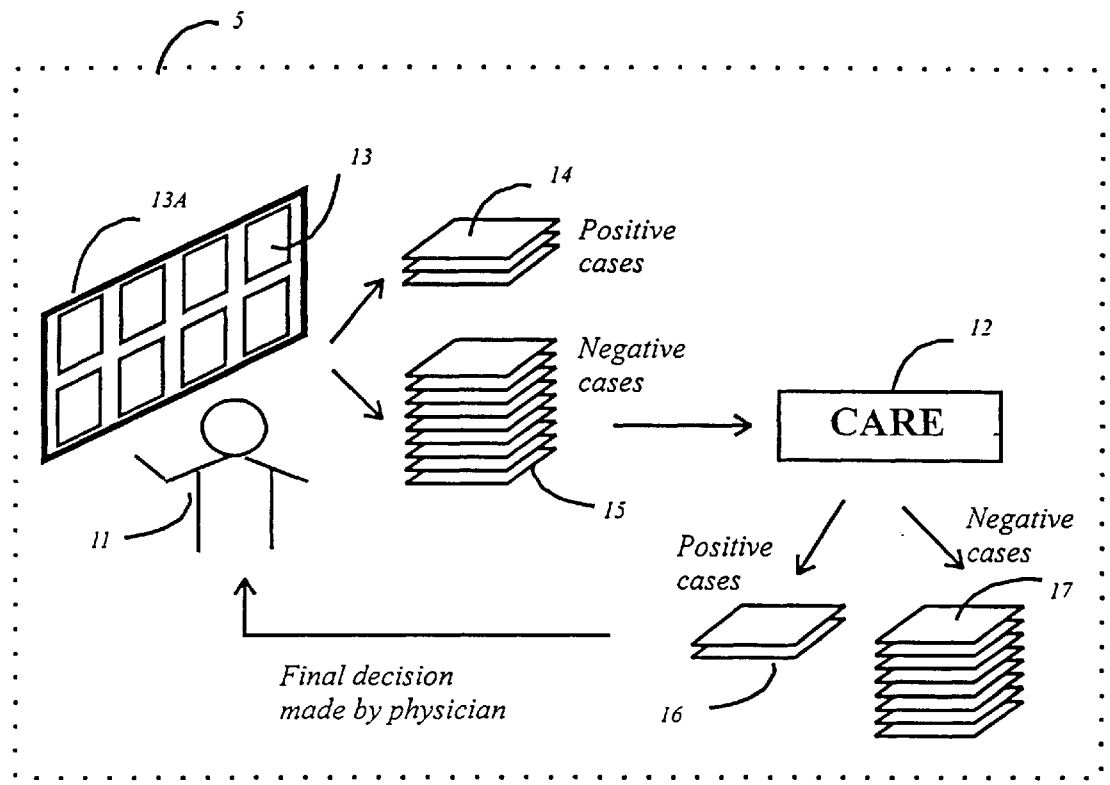
FIG. 1 is a diagram of a process for re-screening lung nodules for the detection of lung cancer.

FIG. 1 illustrates the diagnostic step which improves the detection of suspect nodules. The patients' chest X-ray films 13 are first mounted in a lightbox 13A in a radiological setting. A physician examines the films 13 to determine the existence of suspect lung nodules in the films 13. Films determined by the physician to contain suspect nodules are set aside as positive films 14 for further radiological diagnosis. Negative films 15 determined by the physician to contain no suspect nodules are sent to a computer aided re-screen (CARE) system 12 of the present invention for further detection.

The CARE system 12 is a computer-based system involving multiple stages of processing. Two types of cases are determined by the CARE system 12: positive cases (or "review"cases) 16 and negative cases (or "non-review" cases) 17. The positive cases 16 are sent back to the physician for final decision based on the chest X-ray films.

The method and procedure of present invention can be utilized in two modes: (1) the batch mode where radiological staff collects a set of negative films to process in CARE 12; and (2) the interactive mode where a physician runs the negative film through CARE 12 immediately after the physician makes an initial diagnosis.

Figure 2:
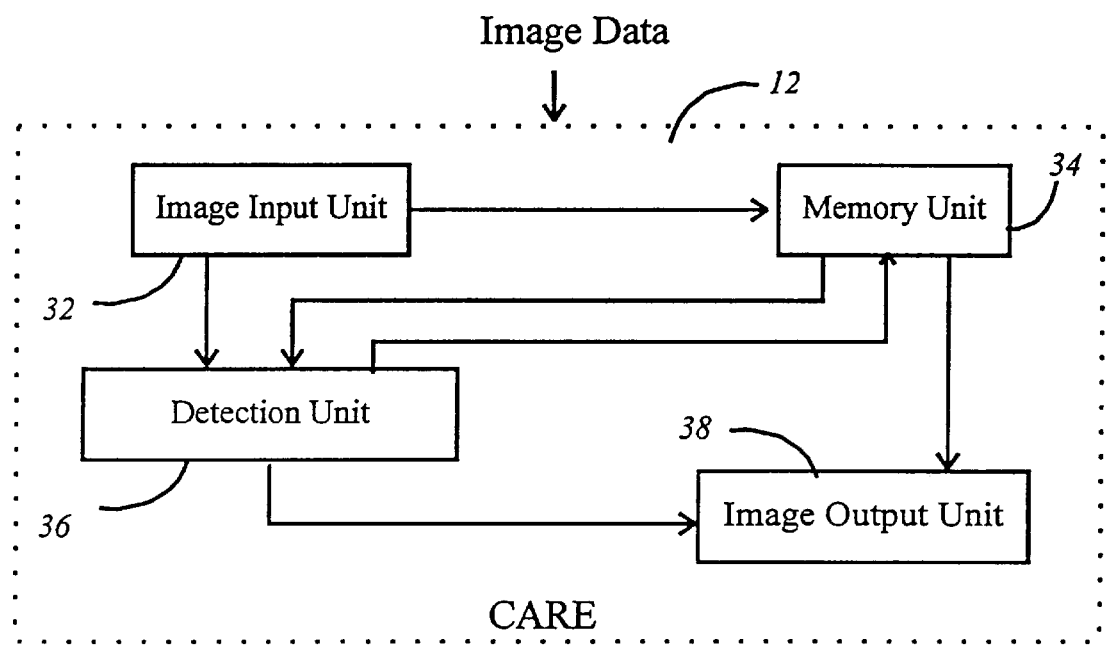
FIG. 2 is a block diagram of a process used by a re-screening unit forming part of the computer aided re-screening (CARE) unit of FIG. 1.

FIG. 2 illustrates a CARE system 12 for digital processing of radiological images according to the present invention. Although the system 12 and method of operation will be described herein in relation to the automated detection and re-screening of lung nodules in radiological chest images using digital image processing, multi-resolution processing, and artificial neural networks, it should be understood that the system 12 and its method of operation my be used in numerous other digital image processing applications.

Using the system 12, image data of an anatomic region of interest, such as a chest (not shown), is entered into an image input unit 32. The input data may be provided for example by a video camera, computer radiograph (CR) system, direct digital radiography (DDR) system, picture archive and communication (PACS) system, or a film digitizer. The data in the image input unit 32 is stored for later retrieval and use in a memory unit 34, or sent to an detection unit 36. Any suitable memory unit device 34, such as magnetic tape, computer disk, optical laser storage, etc., can be utilized. The detection unit 36 applies the detection method (which includes the re-screening method to be discussed later) of the present invention to the input image to detect lung nodules within the image. As will be described later in greater detail, the detection unit 36 includes multiple phases that generally correspond to the several main steps of the detection method of the present invention. Subsequently, the image is sent to the memory unit 34 for storage and/or to an image output unit 38 such as a monitor, a printer, a plotter, a chart recorder, or the like.

Figure 3:
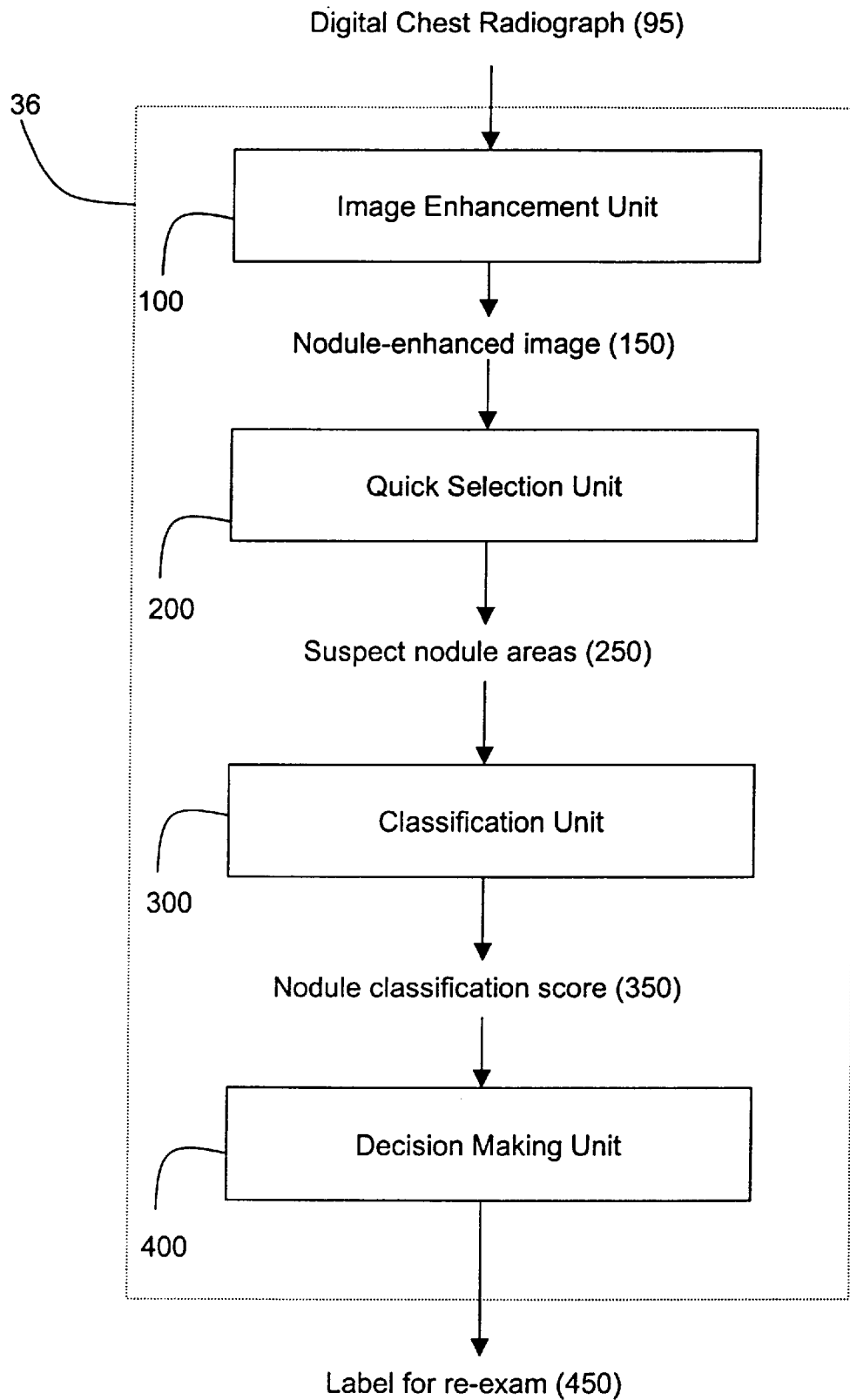
FIG. 3 is a block diagram of an detection unit forming part of the system of FIG. 2.

With reference to FIG. 3, the detection unit 36 generally includes multiple phases or stages. In the first phase, an image enhancement unit 100 performs multi-resolution decomposition and matching in order to enhance the object-to-background contrast in a nodule-enhanced image (150).

In the second phase, a quick selection unit 200 performs sphericity testing of smaller regions in a series of sliced images, and several suspect nodule areas (SNA) are then segmented and selected, in order to identify suspect areas (for example 32×32 pixels) 250, which may include abnormalities (i.e., nodules)

During the third phase, a classification unit 300 employs feature extraction, feature pattern classifier, image area classifier, and data fusion center processes to determine the classification scores (350) of SNA at each location.

During the fourth phase, a decision making unit 400 employs occurrence evaluation, fraction determination, classification threshold determination, and reviewing thresholding to select small portion of positive films labeled for re-exam (450) for physician further reviewing.

Having briefly described the four phases of the detection unit 36, a more detailed description will follow. As shown in FIG. 3, a digital chest image 95 is fed to the image enhancement unit 100. While digital radiographs are becoming more readily available, typically chest images are obtained with screen-film (X-ray) technology. In the event an X-ray film is presented for automated processing, a digitized chest image is acquired by digitizing clinical X-ray chest films, by direct digital radiography (DDR) system, PACS, or by using a Computer Radiography (CR) system. Digital chest images possessing pixels in an approximately the 100–200 μm resolution range and having 4096 gray scale levels are first acquired. A simple contrast scaling function such as window leveling, is used to obtain a constant contrast between the lung space area and the mediastinum area. Each pulmonary image is subsequently reduced to 500×512×12 bits (for example, by averaging a 2×2 pixel region) for use with the system 12, and is periodically obtained using the latter technique.

Figure 4:
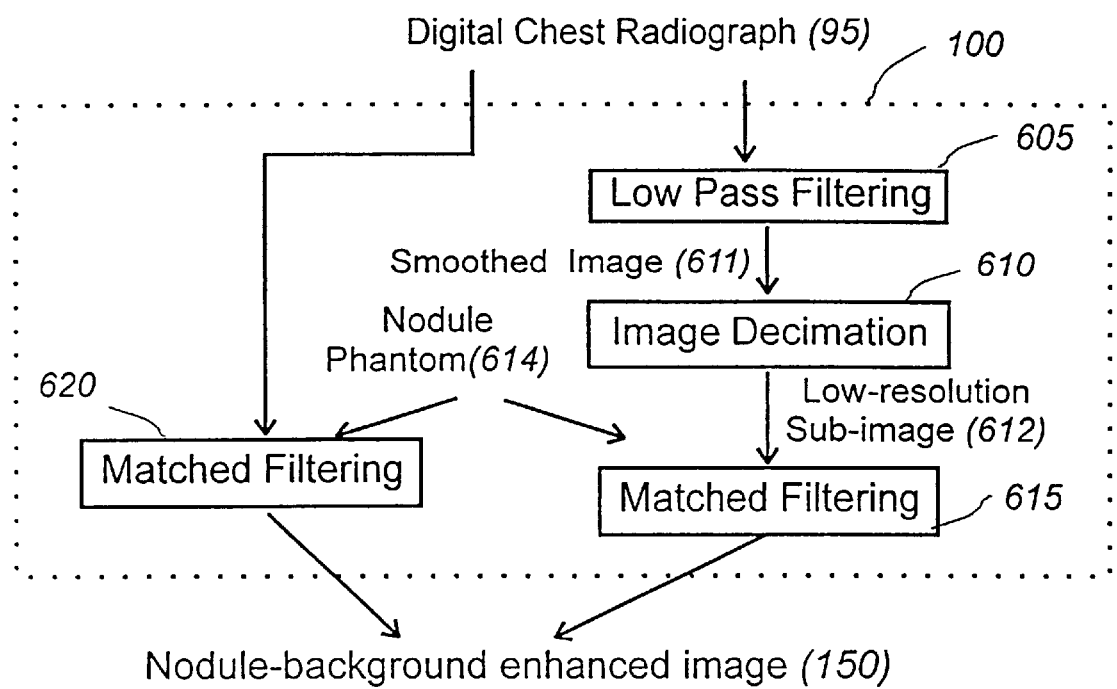
FIG. 4 is a block diagram of an image enhancement unit forming part of the detection unit of FIG. 3.

Potential nodule information in a radiograph is enhanced by a multi-resolution match filtering technique in image enhancement unit 100, illustrated in FIG. 4. First, a low pass filter 605 is applied to the digital chest image 604 followed by image decimation unit 610 in order to obtain a low-resolution sub-image 612. The size of the low-resolution sub-image 612 is smaller than that of the digital chest image 604 because of the processing by the image decimation unit 610. As a result, the size of the nodule suspect in the low-resolution sub-image 612 is smaller than in the digital chest image 604, enabling the use of a single nodule phantom 614 to detect nodules at the original size (in the digital chest image 95) and larger size nodules. The nodules in the low-resolution sub-image 612 have approximately the same size as the nodule phantom 614, since the size of the nodule phantom 614 is taken as a reference in the image decimation process (unit 610), which changes the sizes of the nodules inputted to the unit 610 to approximately match the size of the reference nodule phantom 614.

The low pass filter 605 can be either a spatial filter, spectral filter, or spectral-spatial filter. One example of the spatial filter is a median filter that uses median pixel value as an output pixel value in a central location and subsequently generates a smoothened image. The spectral filter involves the following steps: Fourier transformation that transforms an image into another image in the frequency domain, low frequency cut-off that eliminates the high frequency component of the transformed image, and an inverse Fourier transform that transforms the cut-off image into a resultant smoothened image. The spectral-spatial filter uses a wavelet transformation method employing one or more of the following filters: Laplacian, Gaussian, quadrature mirror filters (QMF), perfect reconstruction QMF filters (PR-QMF), or biorthogonal (BIO) filters to perform the transformation, as described in Lure, F. Y. M., et al, "Multi-Resolution Unsharp Masking Technique for Mammogram Image Enhancement", SPIE, Proceedings for Medical Imaging Processing, Volume 2710 (1996), pages 830–839, which is incorporated herein by reference. These filters are small image templates including different coefficients.

The multiplication of an image with these small templates generates a smoothened image at spectral and spatial domains. The smoothened image is then sub-sampled by a certain interval to generate a low-resolution sub-image by means of the image Decimation unit 610. The sub-image is further processed by means of a matched filtering unit 615 to obtain a nodule-enhanced image at low resolution. The use of the multi-resolution matched filtering approach enables the efficient detection of nodules of different sizes. While one approach would be to use a given size nodule of that particular phantom to detect a nodule size, the present invention describes the use of a single nodule phantom 614 to detect all or most nodule sizes.

The original digital image can be processed by means of a generally similar matched filtering unit 620 to generate a nodule-enhanced image at substantially the original resolution. Matched filtering can be either implemented in the spectral domain or in the spatial domain. The spectral domain implementation involves operations of forward and inverse Fourier transform, matrix conjugation and multiplication between digital chest image (604) and nodule phantom (614). The spatial domain implementation is a correlation operation according to which a nodule phantom is multiplied with an image having a generally similar resolution to the original image or a low resolution sub-image, to generate the nodule-enhanced image. One example to generate nodule phantom is as follows. A spherical profile with diameter of 3 mm as well as contrast between the center of nodule phantom and its border is used to synthesize the ideal nodule image along with its surrounding anatomic background for the nodule phantom. Such nodule phantom contains information of a typical nodule and its neighborhood.

The multi-resolution matched filtering technique enables the detection of nodules at different sizes and the reduction of searching time. The matched images at the original resolution are the resultant images with 3-mm nodules enhanced. As the resolution becomes coarser, suspicious nodules with larger sizes will be detected. With reference to FIG. 4, the image decimation unit 610 performs the sub-sampling of the smoothened image and generates a low-resolution sub-image as its output. The size of the nodule in the low-resolution sub-image is equal to the size of the larger nodule in the original image. As a result, when the resolution becomes coarser, the suspicious nodules having larger size with be detected.

Figure 5:
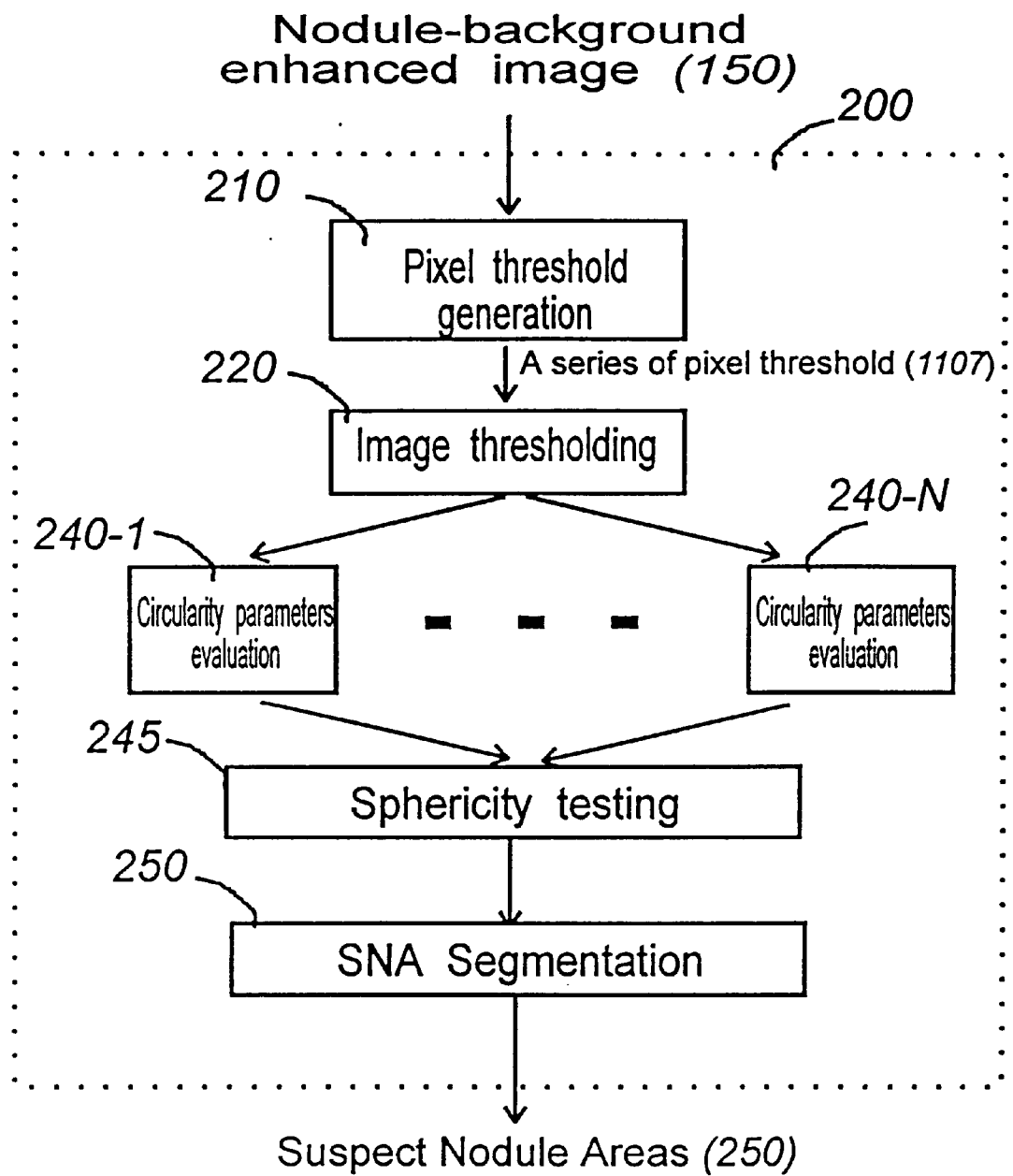
FIG. 5 is a block diagram of a quick selection unit forming part of the detection unit of FIG. 3.

With reference to FIG. 5, the nodule-enhanced image generated by the image enhancement unit 100 is processed based primarily on a typical nodule shape, such as a spherical shape, in quick selection unit 200. A sphericity test is performed at unit 240 and 255 by examining the sphericity parameters of a region at different sliced threshold images in unit 220 with a series of pixel threshold values, generated in unit 210.

The pixel threshold value (1107) is critical to the successful selection of most true nodules in the image since it affects the number of suspect area in each sliced image. Choice of series of pixel threshold value (1107) primarily based on fixed intervals of a cumulative distribution function (CDF) (e.g., 97%, 94%, 91%, etc.) may result in miss of true nodules due to large interval of CDF or in excessive processing time due to the exhaustive threshold processing for sphericity test in each sliced image.

Figure 6:
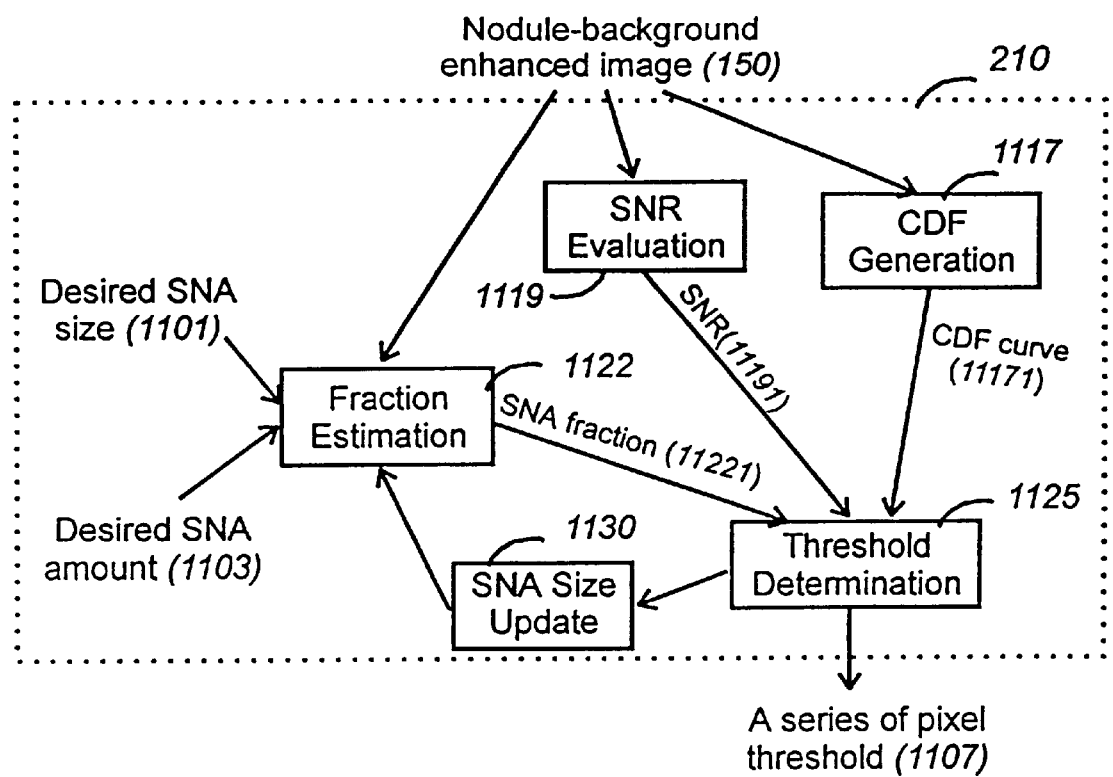
FIG. 6 is a block diagram of a pixel threshold generation unit forming part of the quick selection unit of FIG. 5.

With reference to FIG. 6, the pixel threshold generation unit 210 forming part of quick selection unit 200 of FIG. 5 is based upon the characteristics of desired SNA size 1101, desired SNA amount 1103 and nodule enhanced image (150). Nodule enhanced image (150), desired SNA size 1101 and desired SNA amount 1103 are fed into fraction estimation unit 1122 to determine the SNA fraction 11221 over entire image pixels containing a potential SNA without any false positives. Mathematically, this may be expressed as $$SNA\ Fraction = (desired\ SNA\ size) \cdot (desired\ SNA\ amount)/(total\ pixels\ of\ enhanced\ image).$$

The SNA fraction 11221 is then sent to threshold determination unit 1125. Nodule enhanced image (150) is also fed into SNR evaluation unit 1119 and CDF generation unit 1117. In SNR evaluation unit 1119, signal-to-noise ratio (SNR) 11191 of the image (150) is computed. One method to compute SNR is to compute the ratio of mean pixel value to the standard deviation of the pixel value in the chest region. The SNR value 11191 allows the consideration of signal (nodule) and noise (extraneous background) when evaluating the more realistic fraction of SNA area over an entire image. The SNR value 11191 is fed into threshold determination unit 1125.

In CDF generation unit 1117 of FIG. 6, a histogram and its cumulative distribution function (CDF) curves 11171 are generated over the entire nodule-enhanced image 150. Each point (CDF value) along the CDF curve 11171 represents an integrated percentage of a pixel value in the nodule-enhanced image. Given any CDF value (such as SNA fraction 11221), a corresponding pixel value can always be selected in the unit 1125. In other words, use of SNA fraction 11221 as a CDF value enables the selection of a corresponding pixel value as pixel threshold 1104. Several different pixel values (code values) can be chosen based on the CDF curve 11171 in threshold determination unit 1125. For example, in the beginning, image pixel value with CDF of 97% is selected as a first threshold since the pixel values of true nodules mostly reside in such a range (top 3%) along with a certain number of false positives, which is then considered as desired SNA amount 1103. The SNA fraction 11221 is determined from the desired SNA size 1101, amount 1103, size of enhanced image, and SNR value.

In the threshold determination unit 1125, the CDF threshold can be obtained from [100%−{(SNA size 1101×SNA amount 1103)×(SNR÷1)/(Size of enhanced image)×100%}]. The next level of CDF threshold is obtained by changing the SNA size 1101 in unit 1130 and then performing the evaluation in units 1122, 1119, 1117, and 1125. From the thresholds CDF, a sequence of pixel threshold 1107 are generated by using the CDF curve 11171 in unit 1125. With this method, the CDF values at different levels are not evenly selected.

The difference between the method to obtain pixel threshold values in the present invention and the method with fixed CDF intervals used in the prior art is that the present invention is able to incorporate larger SNA in an efficient method without loss of sensitivity. Additionally, the use of even-interval CDF values would result in the loss of true nodules due to a coarse CDF interval or in the lengthy processing time due to a fine CDF interval.

In the unit 220 of FIG. 5, ten different code values are selected based on their corresponding probabilities in CDF as threshold values to generate 10 different binary thresholding images with code value 1 indicating that such pixel with a covalue 1 in a different image is greater than the threshold value (unit 220). Slicing the image containing detected suspect nodules into 10 different thresholding binary images permits the analysis of a 3-D sphere (alternatively, a 3-D oval) as a plurality of superimposed two-dimensional (2-D) circles with different sizes.

Several isolated islands (i.e., grown regions) then appear in each thresholding image with covariance 1. As the threshold value increases, the region becomes smaller. A combination of grown regions in different thresholding images can be detected for each suspect nodule.

A sphericity test procedure (unit 245) is performed on each thresholding image by examining several parameters including the effective radius (r) of the circular of the SNA, the circularity (C) of SNA, the irregularity (Ir) of the SNA at each thresholding image in unit 240-1, 240-2, . . . 240-N, where N is number of threshold images (e.g., N=10). Combination of the circularity parameters from the same SNA at different thresholds/sliced images gives the sphericity parameters.

The SNAs are selected as nodule candidates if the values for sphericity parameters of the SNA are within a predefined threshold range, for example, in at least 7 out of 10 threshold images. The center of gravity of the suspect nodules is calculated, and once the center of gravity is determined, the selected nodule candidates are then segmented typically into 32×32 image blocks, or approximately 9 mm$^2$ area (unit 250 of FIG. 5), around the center of gravity, for input to the classification unit 300. As used herein, the sum of all the coordinates within the grown regions are averaged to obtain the center of gravity of the suspect nodule.

After the first two processing phases (image enhancement of FIGS. 3, 4 and the quick selection of FIG. 5) on one radiograph, many suspect nodules in the original image (i.e., the input to the detection unit 36 of FIG. 2) and the nodule-enhanced image blocks (i.e., the nodule enhanced image outputted by the image enhancement 100 of FIG. 2), for example, 32×32 pixels, are obtained for further development and application of various types of classification of true or false nodules based on the classification score 350. As used herein, a true nodule is a nodule that has been determined to be an early stage cancerous lesion or symptom, and false nodule refers to a suspect nodule that has been determined to be free of cancer. The suspect nodules are classified by the classification unit 300 of FIG. 7 in order to determine the nodule classification score 350. Based on the score 350, a true or false nodule can be determined.

The classification unit 300 of FIG. 2 will now be described with reference to FIG. 7. The classification unit 300 processes the suspect nodule area 250 in the feature extraction unit 3010, feature pattern classifier 3015, image area classifier 3020, and a data fusion center 3030 to generate the classification score 350 indicating the possibility of the true nodule for this particular SNA 250. This implementation demonstrates that classification of an image can be conducted in two ways (classification based on abstract derived feature parameters and classification based on image area). The classification results can be combined to obtain optimal results via consideration of the performance of each classifier in the data fusion center. Combination of unit 3010 and 3015 is a pattern classification approach in which input image is first converted into feature parameters in feature extraction unit 3010, and then feature pattern classifier 3015 performs classification based on derived features. Such feature parameters can be amplitude and orientation of image edge as shown in the prior art and for any other texture parameters (such as mean, standard deviation, etc.). Usually, the size of feature parameters is much smaller than the size of image area; hence, the feature parameters are independent of image size. Such properties allow a smaller classification architecture and also enable the training of classifiers more quickly than with the use of the entire image area. Instead of classification on abstract feature parameters in unit 3010 and unit 3015, unit 3020 performs classification directly on the image block.

The image area classifier 3020 internally performs feature extraction followed by pattern classification. The image area classifier reads an entire image then performs the classification. Usually, the training is lengthy, but this approach does not miss small subtleties in the image. The feature extraction performed inside the image area classifier may extract some useful features ignored during the traditional feature extraction techniques. The data fusion center 3030 takes detection results from various classifiers (for example, units 3015 and 3020) to arrive at final detection results, a classification score 350 to represent the likelihood of each class (i.e., true or false positive nodule). Unit 3015 is implemented based on a Bayesian decision rule that the classifier with better performance contributes more significantly in the final decision making whereas the classifier with worse performance has less impact in the final decision making. The contribution from each classifier is quantitatively determined based on the detection accuracy and false alarm rate for each classifier.

Figure 7:
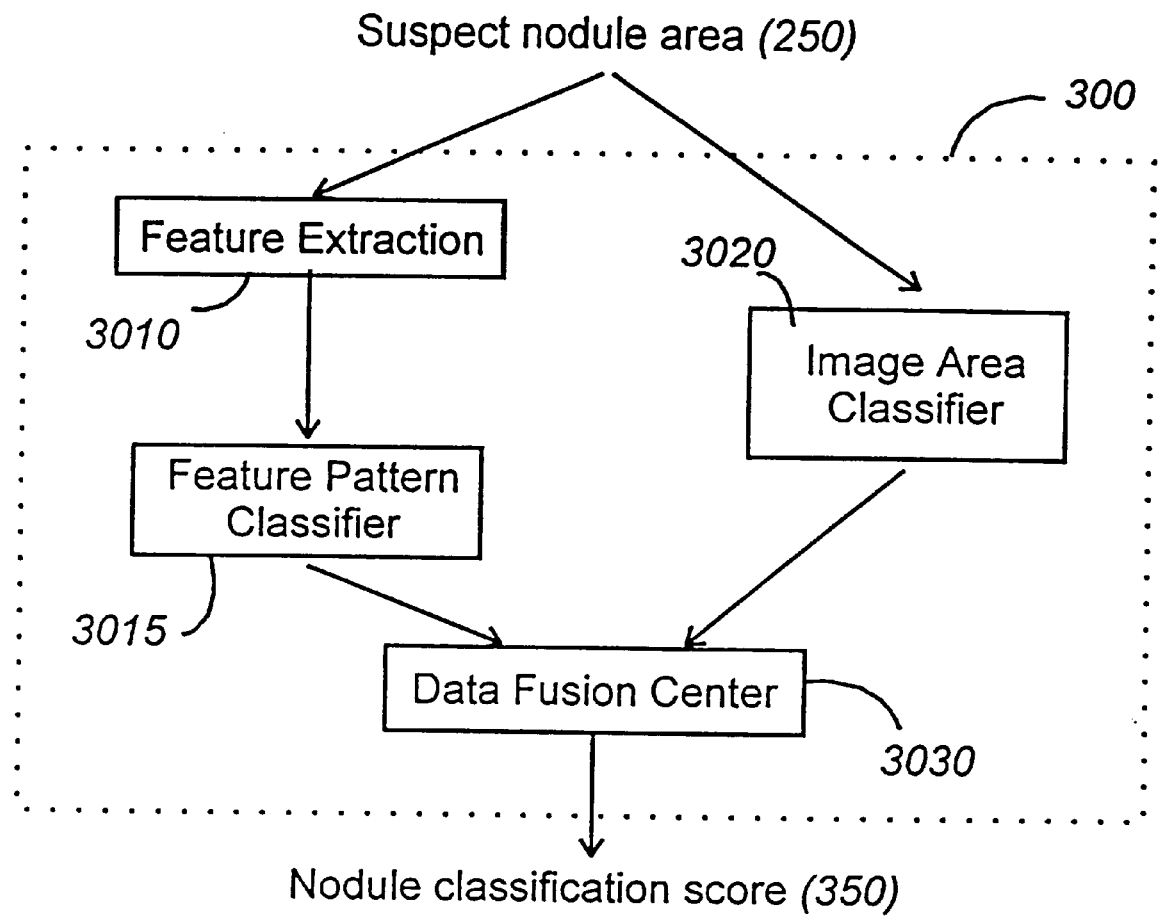
FIG. 7 is a block diagram of a classification unit forming part of the detection unit of FIG. 3.
Figure 8:
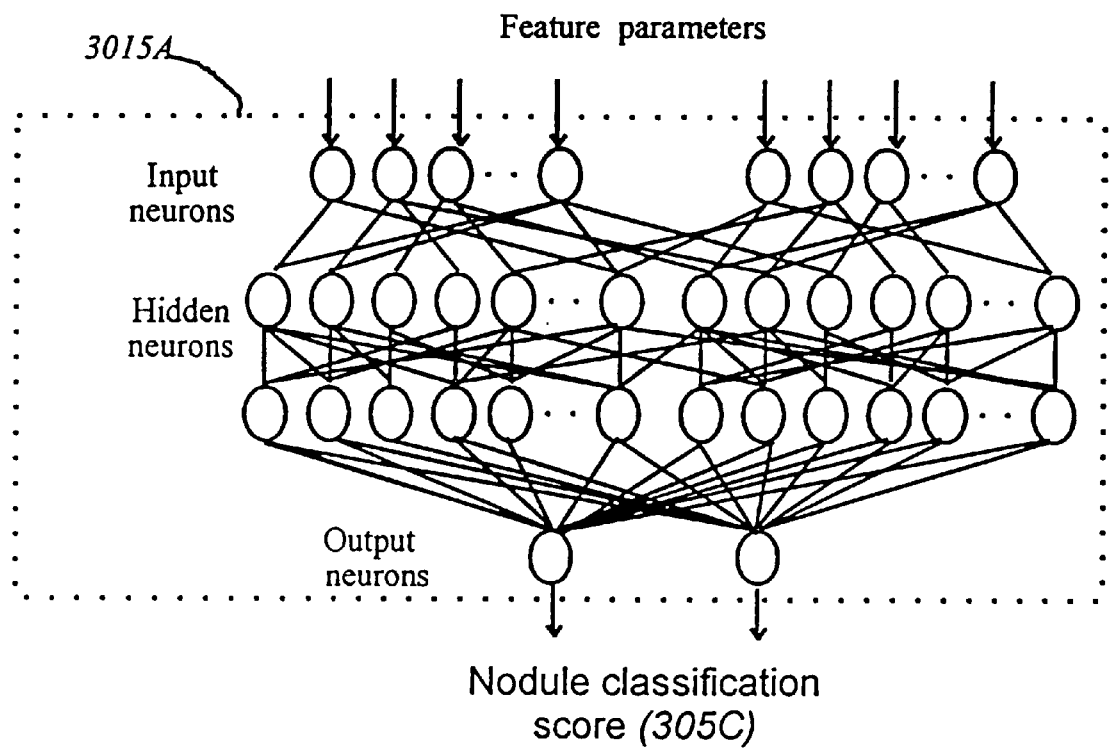
FIG. 8 illustrates the architecture of a back propagation trained feed forward neural network classifier forming part of the classification unit of FIG. 7.

FIG. 8 illustrates an example of the implementation of a feature parameter classifier using the architecture of the back-propagation (BP) artificial neural network (ANN) classifier implementing the feature pattern classification process (unit 3015) in FIG. 7. The BP ANN classifier is trained with a given pattern and the desired target until the error between the desired target and the predicted target are minimum. The trained BP ANN is then used to perform classifications as described in Hertz, J., et al., "Introduction to the Theory of Neural Computation", published by Addison-Wesley Publishing Company, pages 115–120 (1991), which is incorporated herein by reference.

This particular architecture in unit 3015A of FIG. 8 is formed of four processing layers: an input layer, two hidden layers, and an output layer. Each layer is fully connected between its antecedent and succeeding layers. The input layer includes neurons corresponding to the number of feature parameters outputted from feature extraction unit 3010 of FIG. 7. The two hidden layers contain any number of neurons depending on the training results. Two hidden layers are chosen since a multiple hidden-layer back propagation neural network is able to perform any kind of pattern recognition problem. A two-neuron output layer is used to classify either true positive or false positive nodules (presence of absence of nodules). A sigmoidal transfer function, varying from −1 to +1, is used as an activation function in each neuron.

The BP ANN classifier is trained and tested by having a data set of 32×32 image blocks containing various anatomic classes separated into a training set and a test set. The BP ANN learns form the training set presented to it during the learning phase (weight adaptation) until most of the training cases are learned properly. The trained BP ANN is then applied to the test data set. One portion of the data set is used as training examples, whereas the rest of the data set is used as a test set. After training of the BP ANN is complete, entire data sets are then applied to the feature parameters to generate output values ranging from −1 to +1 at each of the two output neurons, representing the possibility of the occurrence of true or false nodules.

Figure 9:
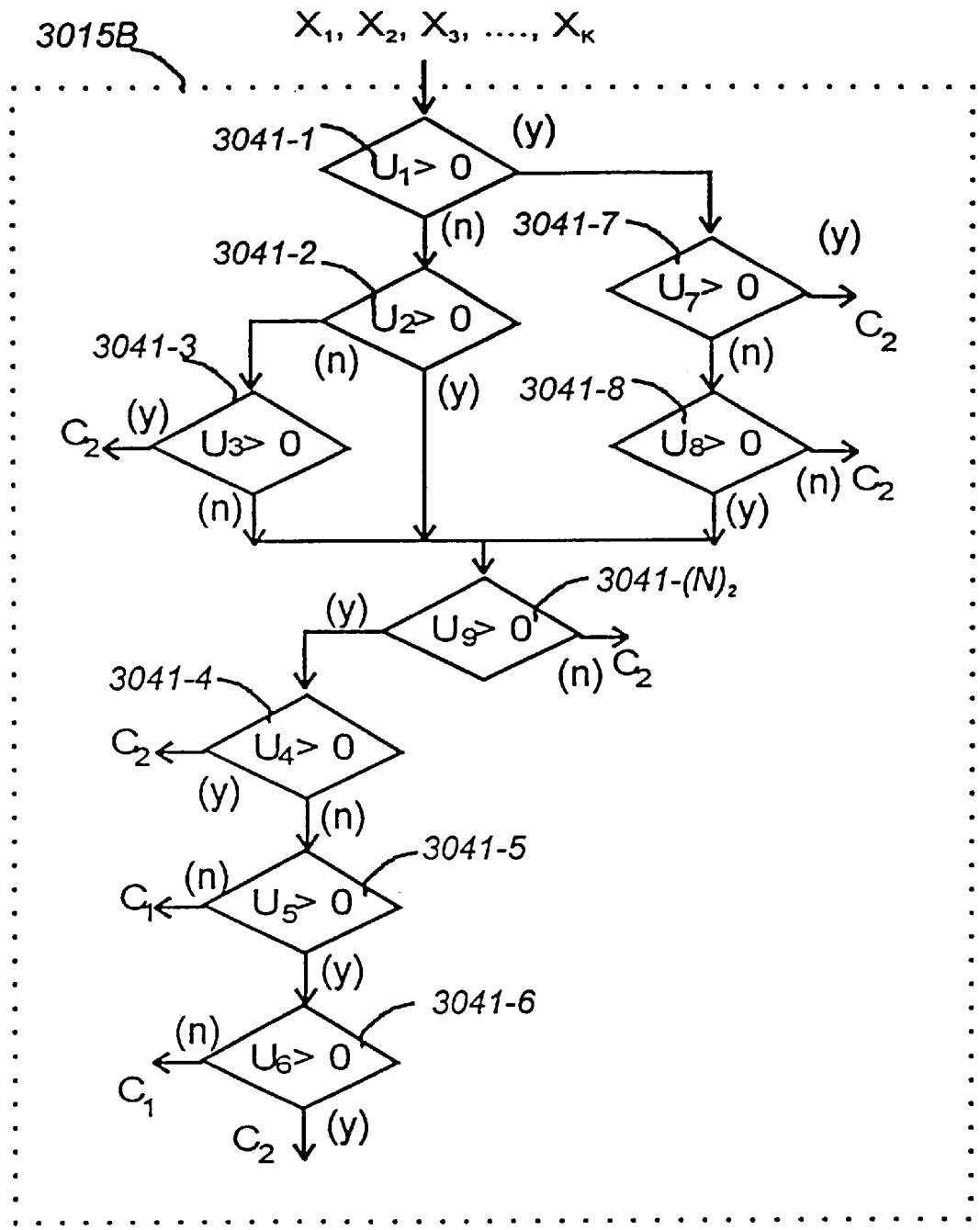
FIG. 9 illustrates the binary decision tree classifier forming part of the classification unit of FIG. 7.

Alternatively, the feature pattern classifier 3015 is implemented by a binary decision tree classifier 3015B of FIG. 9 based on a heuristic decision rule. The heuristic decision rule is a decision criterion that was determined through experience and experiments. The heuristic decision rule is essentially a multiple-branch sequence of conditional determinations. This sequence of multiple conditional determinations can be simplified into a binary decision tree classifier. Also, any complicated operations in the decision node can be simplified into a linear operation. Usually, the binary decision tree classifier 3015B is composed of node operation (U) and branch operation (→). The binary decision classifier 3015B first takes K inputs $X_1, X_2, \ldots, X_k$, each branch node (3041-1, 3041-2, . . . , 3041-N$_2$) performs linear processing ($U_1, U_2, \ldots U_{N2}$), and generates $N_3$ terminal outputs (output of node operation that does not travel into any branch node) which indicate the output of each decision branch. Inputs $X_2, \ldots X_k$ can be the feature parameters derived in the feature extraction unit 3010 of FIG. 7. The final classification results (C1 or C2 indicating true or false nodule) are obtained while combining the identical results from different terminal outputs ($C_1, C_2, \ldots, C_{N3}$).

The binary decision tree classifier 3015B involves two major processing components: linear operation ($U_1, U_2, \ldots$) inside each branch node (3041-1, 3041-2, . . . 3041-N$_2$) and branching operation (→) from one node to another node. The linear operation in all nodes (for example, $U_1=a_1*x_1+a_2*x_2+\ldots$) is usually a matrix operation. The branch operation (→) is based on whether the pre-determined decision criterion (U>0) in each node is satisfied (y) or not (n). Each node operation does not involve all the inputs and each branching operation does not involve travelling all the nodes as shown in FIG. 9. The binary decision classifier is a sequential classification architecture such that once the decision criterion U has been processed, that criterion will never be re-evaluated unless an additional branch is created. Hence, a sequential classification does not allow the later branch operation and node operation to change the decision made in an earlier branch. The output of the binary decision tree at each terminal output is an integer indicating the existence or absence of a particular class.

Figure 10:
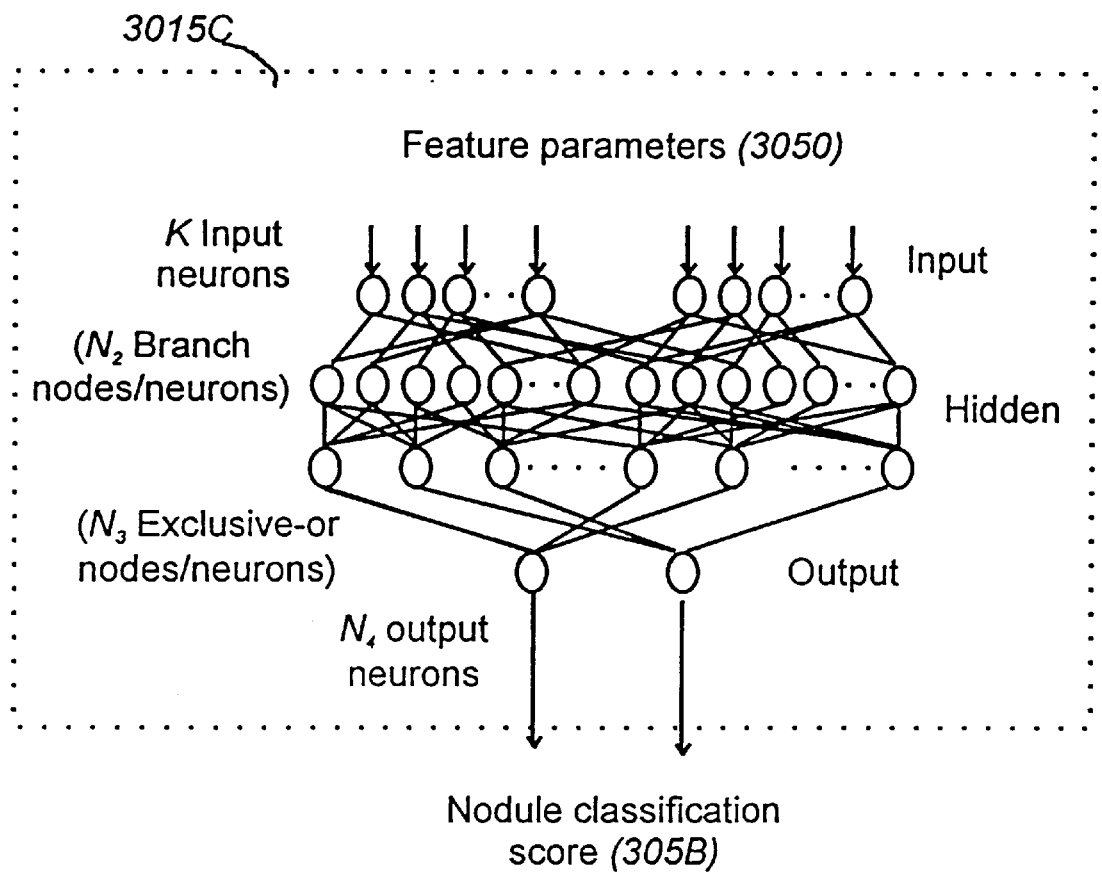
FIG. 10 illustrates the architecture of a decision-tree based pruned neural network classifier forming part of the classification unit of FIG. 7.

A four-layer (one input, two hidden, and one output layers) neural network architecture 3105C of FIG. 10 is utilized to implement the binary decision tree classifier 3015B of FIG. 9. Conventionally, the architecture (processing layers, number of neurons, and connections) to a neural network trained with the back propagation technique in the prior art is ever-changed during the development stage, and the final architecture is obtained once the neural network is trained "successfully" whereas the neural network architecture 3015C is fixed. The number of neurons in the input layer is the same as the number (K) of input $X_1$, $X_2, \ldots X_k$, in binary decision tree classifier 3015B. Neurons in the first hidden layer correspond to the operations in $N_2$ branch nodes (3041-1, 3041-2, . . . 3041-N$_2$) of FIG. 9. Neurons in the second hidden layer correspond to the operations in the $N_3$ terminal outputs from the binary decision tree classifier 3015B. The number of neurons in the output layer corresponds to the desired classes of the detection. In this invention, there are two output neurons corresponding to true and false positive nodules.

Instead of fully connected weights between antecedent and succeeding layers as in conventional neural network architecture (for example, Unit 3015A of FIG. 8), some of the connections between each layer are pruned (not fully connected between two layers) in 3015C of FIG. 10. The reason for the use of a pruned neural network architecture to implement the binary decision tree classifier in 3015B of FIG. 9 is that not all the input variables are used in each node operation (3041-1, 3041-2, . . . , 3041-N$_2$), and each of $N_3$ terminal outputs does not involve branching operation over all the nodes. The second reason for the use of a pruned neural network architecture to implement the binary decision tree classifier in 3015B of FIG. 9 is that the decision of detection output is derived from the terminal output, and each terminal output only contributers to one single detection output.

The connections between the input neurons and neurons in the first hidden layer shows the node operation as a linear function of several inputs. Only inputs used in that node operation will be fed/connected into such a node, and nodes not used in that operation are not connected. The condition statement (>0) is implemented by a hard-limiter. However, a sigmoid function or other continuous non-linear function may also be used to generate robust results with analog values indicating the classification scores. The connections between the neurons in the first and second hidden layers are derived from the logic circuit operation between the node operation and terminal output, namely, terminal output as a function of several nodes. Connection is made if the terminal node is a function of branch node; otherwise the weight/connection is pruned. The weight between the second hidden layer and outputs layer is simply a combination of several terminal output into a desired output.

The initial weights (connections) are determined from the heuristic threshold used in binary decision tree classifier 3015P in FIG. 9. A nonlinear function, such as a hard limiter with binary output (−1 and 1), is utilized in each hidden neuron. This pruned neural network architecture is further trained with the same SNA image sets and their feature parameters described above by using a back propagation training scheme. This neural network only requires a few epochs for complete training since it is not fully connected and the initial weights are derived from an experiential heuristic rule that may be close to the optimal values.

Figure 11:
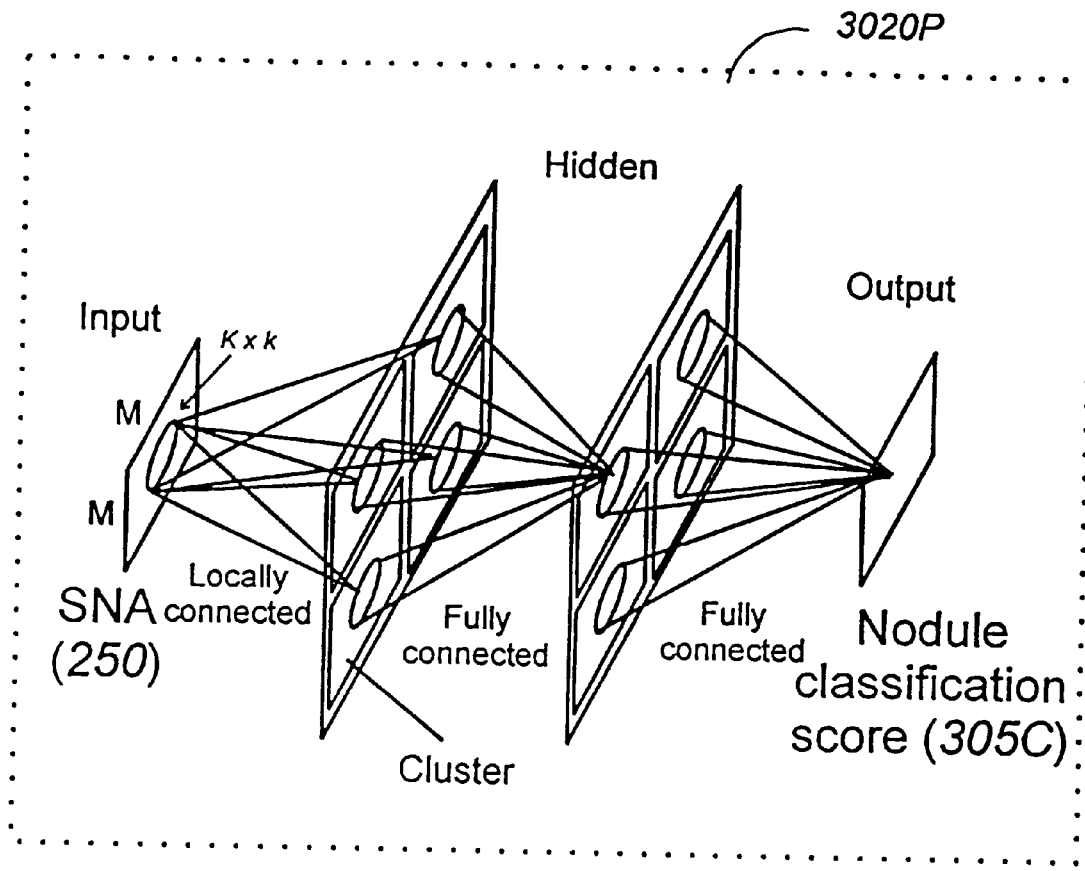
FIG. 11 illustrates the architecture of a convolution neural network classifier forming part of the classification unit of FIG. 7.

FIG. 11 illustrates a convolution neural network (CNN) architecture implementation in unit 3020 of FIG. 7 forming part of classification unit 300. One example of the architecture of CNN is a four layer neural network (one input layer, two hidden layers, and one output layer). The input layer consists of $M^2$ neurons that correspond to the M×M preprocessed input image block in this case, th SNA 250. Both hidden layers are composed of n groups of N×N neurons arranged as n independent N×N feature maps, where N is equal to M=k+1 and the k×k area is the receptive field. Each hidden neuron takes input from a k×k neighborhood on the input image block. For neurons in the same feature map that are one neuron apart, their receptive fields in the input layer are one pixel apart. Moreover, each neuron in the same feature map is constrained to have the same set of $k^2$ weights and to perform the same operation on the corresponding parts of the input image. Namely, each neuron is constrained to process exactly the same way over its receptive field. The benefit of constraining the weights enables the network to perform shift-invariant pattern recognition. Thus, the total effect of the operation can be expressed as a two dimensional discrete convolution with the k×k convolution kernel (the receptive field). The feature map is then the output of the input image convolution with the kernel. All neurons in another feature map share another set of $k^2$ weights in the same way. A more detailed description of the CNN can be found in "Artificial convolution neural network techniques for lung nodule detection", by Lo, Lou, Lin, Freedman, and Mun, IEEE Trans. Med. Imag. Vol 14, pp 711–71, 1995.

The squares indicate clusters (i.e., feature maps) consisting of two-dimensionally arrayed neurons. Each cluster corresponds to a feature map image. The circle on each cluster and the cone between clusters represent weight pattern and connection, respectively. The signal flow is calculated by discrete convolution between clusters and weight patterns as in conventional image processing. For the application of reduction of false-positives in lung nodule detection, the CNN was trained by the image blocks of suspected nodules and was configured and tested for each cancer nodule diagnosis based on x-ray images. The CNN was trained by a supervised learning process to function as a feature detector that directly extracts specific features from the 32×32 pixel image blocks of suspected nodules. The CNN was trained by operating directly on the selected images of suspect nodules, rather than on some subspace of pre-identified image features.

Figure 12:
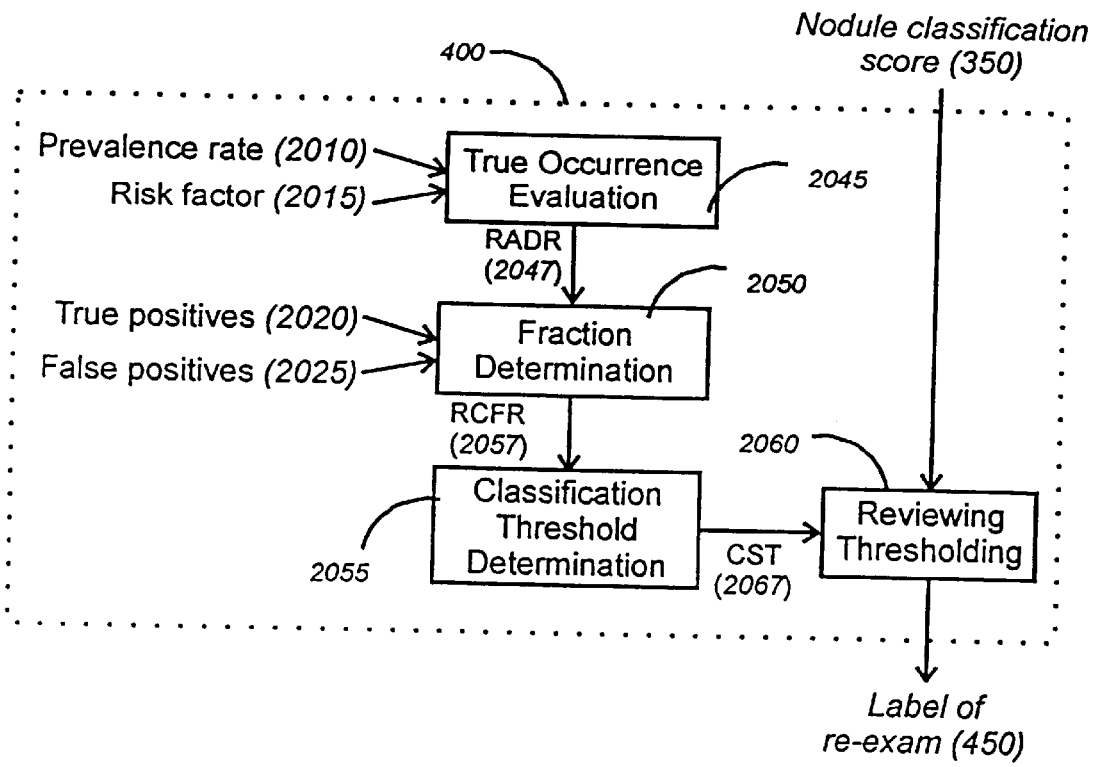
FIG. 12 is a block diagram of a decision making unit forming part of the detection unit of FIG. 3.

FIG. 12 illustrates a decision making unit 400 in FIG. 3 used to select a certain percentage of cases for further review by a physician or by another device, based on the nodule classification score 350. The disease prevalence rate 2010 and risk factor 2015 are first fed into the true occurrence evaluation unit 2045 to determine the risk-adjusted prevalence rate, RAPR 2047 (frequency of the disease for population with risk factor 2015). For lung nodule detection, the prevalence rate 2010 in the U.S. was around 160,000 in 1996, and the risk factor for high-risk population is around 10 times that of the general population. Both prevalence rate and high risk factor change each year and among different types of populations. The RAPR 2047 from unit 2045 and the performance of the detection system (including number of true positives 2020 and number of false positives 2025) are fed into the fraction determination unit 2050 in order to obtain the percentage of the cases for further review, PCFR 2057. The PCFR is obtained by performing the summation of false positives and risk-adjusted prevalence rate 2047. The PCFR 2057 is then fed into the classification score determination unit 2055 to determine the classification score thresholds, CST 2067 (such as circularity, neural network score, etc.). In reviewing thresholding unit 2060, the nodule classification score 350 is further evaluated by comparing the classification score with classification score threshold, CST 2067. Those satisfying the CST 2067 are marked with the label for re-exam 450 that will be sent to a physician for further reviewing.

It should be understood that the methods and systems described herein may be modified within the scope of the invention. For example, while the inventive methods and systems are described herein in connection with the detection of lung nodules, it should be clear that these methods and systems may be used for detecting other types of cancer such as microcalcification clusters or masses in breast cancer, nodules, lumps, irregularities, or tumors in other body parts.

What is claimed is:

1. A system for re-screening an abnormality such as a nodule in a radiological image, the system receiving radiological images identified as negative by previous radiological diagnostic techniques, the system comprising a detection unit comprising:

an image enhancement unit that uses a multi-resolution matched filtering approach to enhance contrast between any abnormalities that may be present and the image background;

a quick selection unit that preliminarily selects a suspect abnormality and uses a pixel thresholding method; and a classification unit that determines a presence and a location of the abnormality and a classification score, and which identifies a false abnormality; and a decision making unit that selects a portion of images for further diagnostic review;

wherein, if a radiological image analyzed by said detection unit is determined to be positive, further radiological diagnosis is performed on it to confirm the existence of a true nodule, and if a radiological image analyzed by said detection unit is determined to be negative, no further radiological diagnosis is performed on it.

2. A system according to claim 1, wherein said multi-resolution matched filtering approach generates low-resolution sub-images with different resolutions from an original image with a plurality of abnormalities of different sizes.

3. A system according to claim 1, wherein said multi-resolution matched filtering approach utilizes a single nodule phantom as a reference.

4. A system according to claim 3, wherein said nodule phantom is correlated with the image to determine likely locations of abnormalities.

5. A system according to claim 1, further including an image decimation unit that generates a low-resolution sub-image, said low-resolution sub-image having a smaller number of pixels than an original input digital image, by discarding redundant image pixels, and said sub-image covering the same area as the original image.

6. A system according to claim 1, wherein said image enhancement unit includes a low-pass filtering unit that smoothes the image.

7. A system according to claim 1, wherein said quick selection unit includes at least one of the following as means for determining threshold values for said pixel thresholding method: a signal-to-noise ratio (SNR) evaluation unit, a cumulative distribution function (CDF) generation unit, a fraction estimation unit, an abnormality size update unit, and a CDF threshold determining unit.

8. A system according to claim 7, wherein said quick selection unit includes said fraction estimation unit, said fraction estimation unit estimating one or more suspect nodule area (SNA) fractions by evaluation the expression, $$SNA\ Fraction=(desired\ SNA\ size)\cdot(desired\ SNA\ amount)/(total\ pixels\ of\ enhanced\ image),$$

where the enhanced image is the output of the image enhancement unit.

9. A system according to claim 7, wherein said quick selection unit includes said CDF threshold determining unit, said CDF threshold determining unit estimating one or more CDF thresholds by evaluating the expression, $$CDF\ Threshold=100\%-[(desired\ SNA\ size)\cdot(desired\ SNA\ amount)\cdot(SNR+1)/(total\ pixels\ of\ enhanced\ image)\cdot 100\%],$$

where SNA is a suspect nodule area and the enhanced image is the output of the image enhancement unit.

10. A system according to claim 7, wherein said quick selection unit uses at least one of the following parameters of an abnormality: a desired SNA size, a desired SNA amount, and SNR of an image.

11. A system according to claim 1, wherein said classification unit receives a suspect abnormality area and determines said classification score for that area, said classification unit comprising:
   a feature extraction unit;
   a feature pattern classifier,
   an image area classifier; and
   a data fusion unit, said data fusion unit integrating detection results from the different classifiers by weighing them.

12. A system according to claim 1, wherein said decision making unit receives said classification score to determine only portions of cases for further review.

13. A system according to claim 1, wherein said decision making unit uses prevalence rate of abnormality, risk factor of abnormality for a certain population, and performance of detection system, including number of true positives and false positives, to determine a classification threshold.

14. A system according to claim 1, wherein said decision making unit comprises:

a true occurrence evaluation unit that evaluates the occurrence of abnormality;
a fraction determination unit that determines a fraction of cases in which abnormality occurs;
a classification threshold determination unit; and
a reviewing thresholding unit that determines whether or not a given image is to undergo further diagnostic review, based on nodule classification score and on the output of the classification threshold determination unit.

15. A method for re-screening an abnormality such as a nodule in a radiological image comprising:
   receiving at least one radiological image, said at least one radiological image having previously undergone diagnostic review;
   identifying said at least one radiological image according to the following rules:
      if said radiological image was identified as positive during said previous diagnostic review, placing the image in a group for further radiological diagnosis to confirm the existence of a true nodule; or
      if said radiological image was determined to be negative during said previous diagnostic review, placing the image in a group for analysis according to a detection method, said detection method comprising the steps of:
         performing an image enhancement step to enhance the contrast between any abnormalities present and image background, said image enhancement step comprising the sub-step of:
            applying multi-resolution matched filtering;
         performing a quick selection step to preliminarily select a suspect abnormality, said quick selection step comprising:
            pixel thresholding;
         performing a classification step to determine a presence and a location of an abnormality and a classification score, and to identify a false abnormality; and
         performing a decision making step to select a portion of images for further diagnostic review, said decision making step including the following sub-steps:
            if said radiological image analyzed by said detection unit is determined to be positive, indicating that further diagnostic review should be performed on it to confirm the existence of a true nodule; or
            if said radiological image analyzed by said detection unit is determined to be negative, indicating that no further radiological diagnosis should be performed on it.

16. A method according to claim 15, wherein said step of applying multi-resolution matched filtering includes the step of generating low-resolution sub-images with different resolutions from an original image with a plurality of abnormalities of different sizes.

17. A method according to claim 15, wherein said step of applying multi-resolution matched filtering utilizes a single nodule phantom as a reference.

18. A method according to claim 17, wherein said step of applying multi-resolution matched filtering comprises the step of correlating said nodule phantom with the image to determine likely locations of abnormalities.

19. A method according to claim 15, further including the step of decimating said image to generate a low-resolution sub-image, said low-resolution sub-image having a smaller number of pixels than an original input digital image, and said sub-image covering the same area as the original image, said step of decimating including the step of discarding redundant image pixels.

20. A method according to claim 15, wherein said step of performing image enhancement includes the step of low-pass filtering to smooth the image.

21. A method according to claim 15, wherein said pixel thresholding step includes at least one of the following steps for determining threshold values: evaluating signal-to-noise ratio (SNR); generating a cumulative distribution function (CDF); estimating a suspect nodule area (SNA) fraction; updating abnormality size; and determining a CDF threshold.

22. A method according to claim 21, wherein said pixel thresholding step includes said step of estimating an SNA fraction, said SNA fraction estimation step estimating one or more suspect nodule area (SNA) fractions by evaluating the expression, $$SNA\ Fraction = (desired\ SNA\ size) \cdot (desired\ SNA\ amount)/(total\ pixels\ of\ enhanced\ image),$$

where the enhanced image is the output of the image enhancement step.

23. A method according to claim 21, wherein said pixel thresholding step includes said step of determining a CDF threshold, said CDF threshold determining step estimating one or more CDF thresholds by evaluating the expression, $$CDF\ Threshold = 100\% - [(desired\ SNA\ size) \cdot (desired\ SNA\ amount) \cdot (SNR+1)/(total\ pixels\ of\ enhanced\ image) \cdot 100\%],$$

where the enhanced image is the output of the image enhancement unit.

24. A method according to claim 21, wherein said pixel threshold determination uses at least one of the following parameters of an abnormality: a desired SNA size, a desired SNA amount, and SNR of an image.

25. A method according to claim 15, wherein said classification receives a suspect abnormality area and determines said classification score for that area, said classification step comprising the steps of:

performing feature extraction;

performing feature pattern classification;

performing image area classification; and integrating detection results from the different classification steps by weighing them.

26. A method according to claim 15, wherein said decision making step receives and classification score and determines only portions of cases for further review.

27. A method according to claim 15, wherein said decision making step includes the step of using prevalence rate of abnormality, risk factor of abnormality for a certain population, and performance of detection system, including number of true positives and false positives, to determine a classification threshold.

28. A method according to claim 15, wherein said decision making step comprises the steps of:

evaluating the true occurrence of abnormality;

determining a fraction of cases in which abnormality occurs;

determining a classification threshold; and applying said classification threshold to determine whether or not a given image is to undergo further diagnostic review, based on nodule classification score.

* * * * *

UNITED STATES PATENT AND TRADEMARK OFFICE
CERTIFICATE OF CORRECTION

PATENT NO.    : 6,125,194
DATED         : September 26, 2000
INVENTOR(S)   : Hwa-Young M Yeh, Yuan-Ming F Lure, Jyh-Shyan Lin It is certified that error(s) appears in the above-identified patent and that said Letters Patent is hereby corrected as shown below:

On the title page item [73],
"Assignee: Caelum Research Corporation,
Rockville, Md."

To, -- Assignee: Deus Technologies, LLC,
Rockville, Md.--

Signed and Sealed this

Twenty-fourth Day of April, 2001

Attest:

NICHOLAS P. GODICI

*Attesting Officer*     *Acting Director of the United States Patent and Trademark Office*